United States Patent
Duan et al.

(10) Patent No.: US 11,076,931 B2
(45) Date of Patent: *Aug. 3, 2021

(54) CAPSULE FOR DETECTION OF GASTROINTESTINAL MOTILITY AND METHOD FOR PREPARING THE SAME

(71) Applicant: Ankon Medical Technologies (Shanghai), LTD., Shanghai (CN)

(72) Inventors: Xiaodong Duan, Pleasanton, CA (US); Hongjiao Song, Dujiangyan (CN); Shaobang Zhang, Hangzhou (CN)

(73) Assignee: Ankon Medical Technologies (Shanghai) Co., LTD., Shanghai (CN)

( * ) Notice: Subject to any disclaimer, the term of this patent is extended or adjusted under 35 U.S.C. 154(b) by 751 days.

This patent is subject to a terminal disclaimer.

(21) Appl. No.: 15/635,212

(22) Filed: Jun. 28, 2017

(65) Prior Publication Data

US 2018/0055597 A1  Mar. 1, 2018

(30) Foreign Application Priority Data

Jul. 27, 2016  (CN) .......................... 201610601158.3

(51) Int. Cl.
| | | |
|---|---|---|
| *A61B 5/00* | (2006.01) | |
| *A61B 90/00* | (2016.01) | |
| *A61K 49/04* | (2006.01) | |
| *A61B 6/12* | (2006.01) | |
| *A61B 6/00* | (2006.01) | |
| *A61K 9/48* | (2006.01) | |

(52) U.S. Cl.
CPC ................ *A61B 90/39* (2016.02); *A61B 6/12* (2013.01); *A61B 6/481* (2013.01); *A61B 6/50* (2013.01); *A61K 9/4866* (2013.01); *A61K 49/0404* (2013.01); *A61K 49/0409* (2013.01); *A61B 2090/3966* (2016.02)

(58) Field of Classification Search
CPC ...... A61K 9/48; A61K 9/4808; A61K 9/4816; A61K 9/4841; A61B 6/12; A61B 5/073; A61B 5/42; A61B 5/4255
See application file for complete search history.

(56) References Cited

U.S. PATENT DOCUMENTS

| | | | |
|---|---|---|---|
| 5,128,140 A * | 7/1992 | Chapura | A61K 9/0065 424/451 |
| 2005/0063906 A1* | 3/2005 | Kraizer | A61B 5/073 424/9.1 |

FOREIGN PATENT DOCUMENTS

| | | |
|---|---|---|
| CN | 101773674 | 7/2010 |
| CN | 101773674 A * | 7/2010 |

OTHER PUBLICATIONS

"Clinical Applied of Radiopaque Marker's Method on Gastrointestinal Motility" Chen Yun, Wang Xueqin, Dai Fei, Zhu Youling. Luo Jinyan. Journal of Practical Radiology Sep. 2001, vol. 17, issue 9. Guangzhou, China.

"Making a radiopaque marker used in the gastric emptying examination" Chin. J. Gastro. Hepa, Aug. 2003, Vol.12, No. 4. Lin Muxian, Zhang Houde, Zhang Hourui, DepartmentofGastroenterology, Nanshan Peoples Hospital, Shenzhen, China.

* cited by examiner

*Primary Examiner* — Micah Paul Young
(74) *Attorney, Agent, or Firm* — Treasure IP Group, LLC

(57) ABSTRACT

A capsule for detection of gastrointestinal motility and a method for preparing such a capsule is provided. The capsule comprises a capsule enclosure and a preset quantity of radiopaque markers filled in the capsule. The radiopaque markers further comprise a solid X-ray contrast agent, a medical plastic with a density of at most at 1.4 g/cm$^3$ and an auxiliary agent.

9 Claims, 3 Drawing Sheets

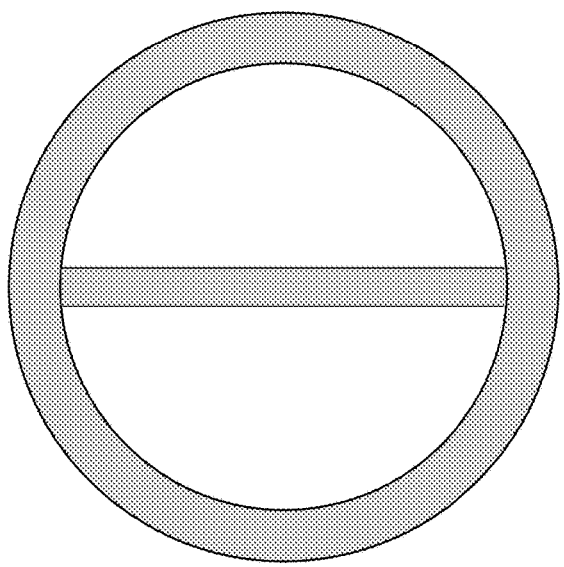
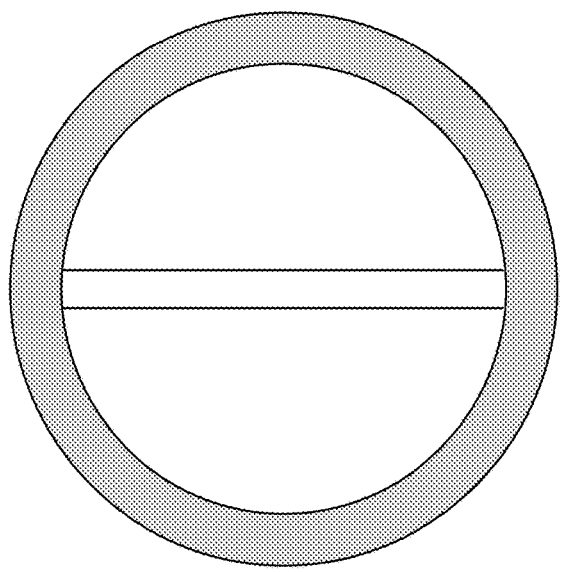
FIG. 6   FIG. 7
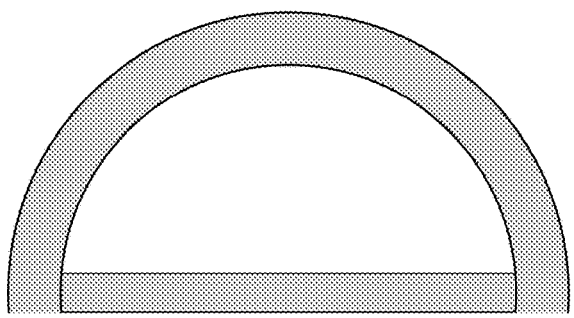
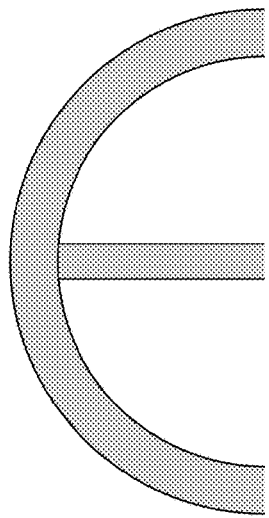
FIG. 8   FIG. 9

CAPSULE FOR DETECTION OF GASTROINTESTINAL MOTILITY AND METHOD FOR PREPARING THE SAME

CROSS-REFERENCE TO RELATED APPLICATIONS

This application claims priority to Chinese Patent Application No. 201610601158.3 filed on Jul. 27, 2016, the contents of which are incorporated by reference herein.

FIELD OF INVENTION

The subject matter herein generally relates to a capsule for detection of gastrointestinal motility, and in particular to a capsule filled with radiopaque markers for detection of gastrointestinal motility and a method for preparing the capsule.

BACKGROUND

Gastrointestinal tract is an important channel for digestion and absorption of human body, so to a large extent, whether its motility is normal or not may affect the human health. Gastrointestinal motility detection comprises detection for gastric motility, small intestinal motility and colonic motility. Manometry, radio telemetry and positron emission tomography are commonly used for gastric motility detection, hydrogen breath test for small intestinal motility detection, and defecography, balloon expulsion test and anorectal manometry for colonic motility detection. The gastric motility, small intestinal motility and colonic motility are detected in different methods. This causes inconvenience in gastrointestinal motility detection as well as an increase of detection cost. Therefore, a capsule that is capable of detecting the gastrointestinal motility with low detection cost and a method for preparing the capsule are needed.

SUMMARY OF THE INVENTION

The present invention provides a capsule for detection of gastrointestinal motility and a method for preparing the capsule, which implements detection by radiopaque markers in the capsule.

In one embodiment of the present invention, the capsule for detection of gastrointestinal motility comprises a capsule enclosure and one or more radiopaque markers filled in the capsule. Each radiopaque marker comprises a solid X-ray contrast agent, a medical grade plastic with a density less than 1.4 $g/cm^3$ and an auxiliary agent.

The solid X-ray contrast agent is selected from barium sulfate, bismuth salt and Tungsten.

When the X-ray contrast agent is barium sulfate, the weight ratio of barium sulfate in the marker is between 20%-40%, the weight ratio of medical grade plastic is between 35%-45% and the weight ratio of auxiliary agent is between 25%-35%; when the X-ray contrast agent is bismuth salt, the weight ratio of bismuth salt in the marker is between 10%-30%, the weight ratio of medical grade plastic is between 45%-55% and the weight ratio of auxiliary agent is between 25%-35%; and when the X-ray contrast agent is Tungsten, the weight ratio of Tungsten in the marker is between 5%-25%, the weight ratio of medical grade plastic is between 50%-60% and the weight ratio of auxiliary agent is between 25%-35%.

The medical grade plastic is selected from Polyvinyl chloride (PVC), Polystyrene (PS), Polyethylene (PE), Polypropylene (PP), Polycarbonate (PC), and Thermoplastic polyurethanes (TPU).

The auxiliary agent is selected from lubricants, plasticizers, heat stabilizers, and/or colorants.

The density range of the radiopaque marker is between 1.0-1.7 $g/cm^3$.

The radiopaque markers are ring shaped markers which come with four shapes of cross sections including O-ring, Double D, Cross and Tri-chamber.

By adjusting the position of solid X-ray contrast agent in the radiopaque markers, the radiopaque markers with same appearance show different shapes under the X-ray.

The capsules for detection of gastrointestinal motility which feature the same shape and show different shapes under the X-ray are used in the segment detection for colonic motility to detect colonic transit function.

The radiopaque markers are ring shaped markers with a cross section of double D which are shown as O-ring, D-ring or E-ring under the X-ray.

In one embodiment of the present invention, a method for preparing the capsule, wherein the solid X-ray contrast agent and the auxiliary agent are added into the medical grade plastic with a density less than 1.4 $g/cm^3$, and through injection molding or extrusion process, the medical grade plastics are made into radiopaque markers and a preset quantity of radiopaque markers is filled into a capsule enclosure to form the capsule for detection of gastrointestinal motility.

The solid X-ray contrast agent is uniformly distributed in the radiopaque markers to form ring shaped markers which have four shapes of cross sections including O-ring, Double D, Cross and Tri-chamber.

The position of solid X-ray contrast agent in the marker can be adjusted to allow the markers with same appearance to show different shapes under the X-ray.

The radiopaque markers are ring shaped markers with a cross section of double D which are shown as O-ring, D-ring or E-ring under the X-ray.

BRIEF DESCRIPTION OF THE DRAWINGS

Exemplary embodiments of the disclosure will be more clearly understood from the following detailed description taken in conjunction with the accompanying drawings in which:

FIG. 6 is an illustration of a top view of a first exemplar radiopaque marker in accordance with a second embodiment of the present invention.

FIG. 7 is an illustration of a top view of a second exemplar radiopaque marker in accordance with the second embodiment of the present invention.

FIG. 8 is an illustration of a top view of a third exemplar radiopaque marker in accordance with the second embodiment of the present invention.

FIG. 9 is an illustration of a top view of a fourth exemplar radiopaque marker in accordance with the second embodiment of the present invention.

DETAILED DESCRIPTION

Figure 1:
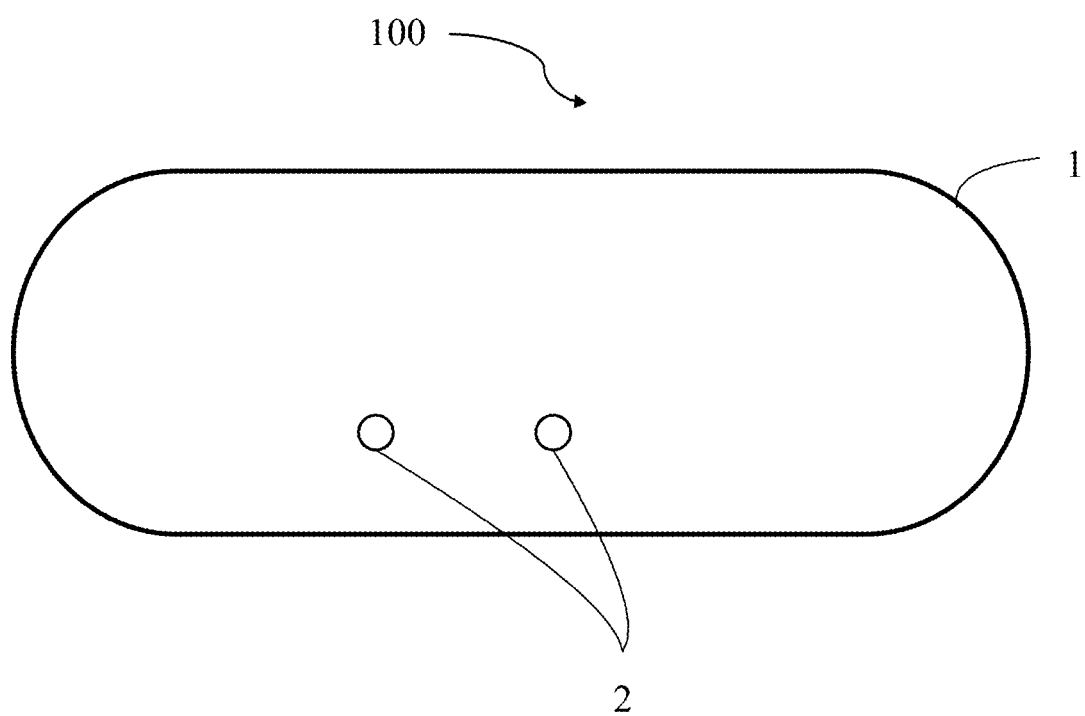
FIG. 1 is a schematic view of a capsule for detection of gastrointestinal motility in accordance with aspects of the present invention.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

The structure and method of using a vibration capsule device is described in detail below. Elements in the drawings are 100 Capsule for detection of gastrointestinal motility
2 Capsule enclosure
3 Radiopaque marker FIG. 1 illustrates a schematic view of a capsule for detection of gastrointestinal motility, wherein the capsule is used to detect the transit function of colon. The capsule for detection of gastrointestinal mobility 100 (detection capsule) comprises a capsule enclosure 1 and a preset quantity of radiopaque markers 2 filled in the capsule enclosure 1 (FIG. 1 exemplifies a capsule enclosure 1 filled with 2 radiopaque markers 2). The capsule enclosure 1 is made of pharma gel or hydroxypropyl methylcellulose with additives (food coloring as an example), including gastric-dissolved capsule, enteric capsule, plant derived capsule, etc. When the capsule enclosure 1 is a gastric-dissolved capsule or plant derived capsule, the capsule enclosure 1 can be used in stomach, small intestine and colon for motility detection. When the capsule enclosure 1 is an enteric capsule, the capsule enclosure 1 can be used in small intestine and colon for motility detection. The preset quantity of radiopaque markers is preset in accordance with clinical efficacy, such 16, 18, 20, 22 or 24.

The radiopaque markers 2 are used to simulate the movement of chyme in the gastrointestinal tract, and detect the motility of stomach, small intestine and colon by examining quantity and location of residual markers therein. The radiopaque markers 2 comprise a solid X-ray contrast agent, a medical grade plastic with a density less than 1.4 g/cm$_3$ and an auxiliary agent. The solid X-ray contrast agent is selected from barium sulfate (BaSO4), bismuth salt and Tungsten, wherein, the bismuth salt is selected from bismuth oxychloride, basic bismuth carbonate and bismuth oxide. The medical grade plastic is selected from Polyvinyl chloride (PVC, 1.4 g/cm$^3$), Polystyrene (PS, 1.05 g/cm$^3$), Polyethylene (PE, 0.95 g/cm$^3$), Polypropylene (PP, 0.92 g/cm$^3$), Polycarbonate (PC, 1.18-1.22 g/cm$^3$), and Thermoplastic polyurethanes (TPU, 1.2 g/cm$^3$). The auxiliary agent is selected from lubricants, plasticizers, heat stabilizers, and/or colorants.

In one embodiment, the weight ratio of the solid X-ray contrast agent, the medical grade plastic and the auxiliary agent in the radiopaque marker 2 is adjusted to make the density of marker 2 as close as possible to the density of chyme in gastrointestinal tract, so as to achieve better simulation effect. In the preferred embodiment, the density of chyme in gastrointestinal tract is about 1.09 g/cm$^3$, and in accordance with such value, the density of the radiopaque marker 2 is set to between 1.0 g/cm$^3$ and 1.7 g/cm$^3$.

When the solid X-ray contrast agent is barium sulfate, the weight ratio of barium sulfate in the radiopaque marker 2 is between 20%-40%, the weight ratio of medical grade plastic is between 35%-45% and the weight ratio of auxiliary agent is between 25%-35%.

When the solid X-ray contrast agent is bismuth salt, the weight ratio of bismuth salt in the marker 2 is between 10%-30%, the weight ratio of medical grade plastic is between 45%-55% and the weight ratio of auxiliary agent is between 25%-35%.

When the solid X-ray contrast agents is Tungsten, the weight ratio of Tungsten in the marker 2 is between 5%-25%, the weight ratio of medical grade plastic is between 50%-60% and the weight ratio of auxiliary agent is between 25%-35%.

In preparation of the radiopaque markers 2, the solid X-ray contrast agent and the auxiliary agent are added into the medical grade plastic which are made into ring shaped radiopaque markers 2 through injection molding or extrusion process. After cleaning and disinfecting, the preset quantity of radiopaque markers 2 is filled into the capsule enclosure 1 and packed and disinfected to form the detection capsule 100 set forth herein.

Figure 2:
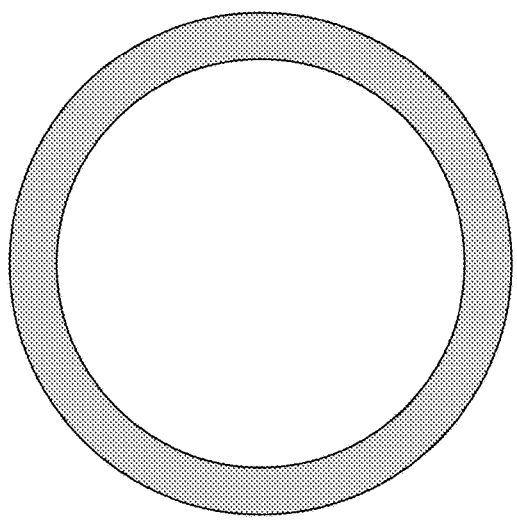
FIG. 2 is an illustration of a top view of a first exemplar radiopaque marker in accordance with the first embodiment of the present invention.
Figure 3:
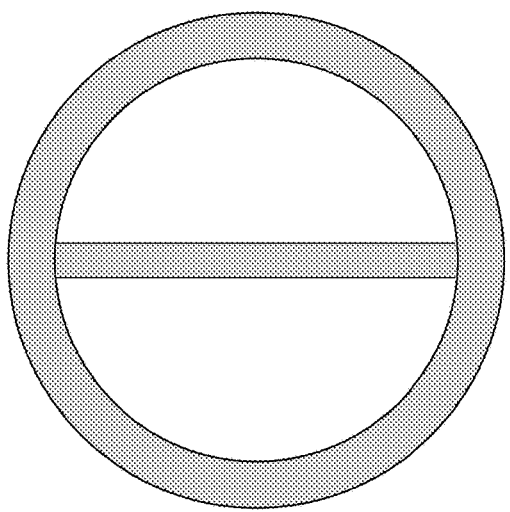
FIG. 3 is an illustration of a top view of a second exemplar radiopaque marker in accordance with the first embodiment of the present invention.
Figure 4:
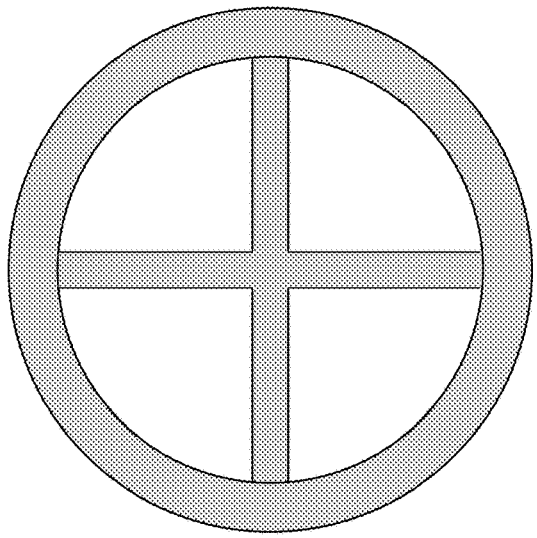
FIG. 4 is an illustration of a top view of a third exemplar radiopaque marker in accordance with the first embodiment of the present invention.
Figure 5:
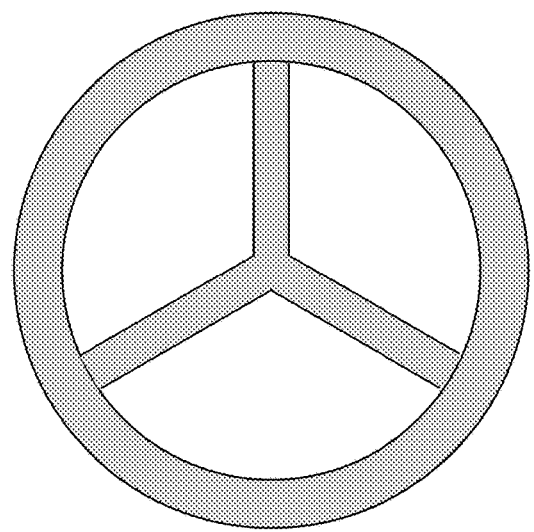
FIG. 5 is an illustration of a top view of a fourth exemplar radiopaque marker in accordance with the first embodiment of the present invention.

FIGS. 2-5 are top views of radiopaque markers. In preparation of the radiopaque markers 2 using injection molding or extrusion process, due to the difference of molds, the shape will be different. For example, the ring shaped radiopaque markers come with various shapes of cross sections, including O-ring as shown in FIG. 2, Double D as shown in FIG. 3, Cross as shown in FIG. 3, Tri-chamber as shown in FIG. 4, etc.

In the preferred embodiment of the present invention, outer diameter (O.D.) of the ring as described above is 4-5 mm, wherein the preferred O.D. is 4.4-4.6 mm and the optimal O.D. is 4.5 mm; inner diameter (I.D.) of the ring as described above is 3.2-3.8 mm, wherein the preferred I.D. is 3.45-3.6 mm and the optimal I.D. is 3.55 mm; thickness of the radiopaque markers having Double D, Cross and Tri-chamber cross-sections is 0.5-1.0 mm, wherein the preferred range is 0.7-0.9 mm and an optimal range is 0.75 mm.

In preparation of the radiopaque markers 2 using injection molding or extrusion process, the solid X-ray contrast agents are uniformly distributed in the radiopaque markers 2, leading to a clear cross section under X-ray. When cross section of the radiopaque markers 2 is shaped as an O-ring shown in FIG. 2, the markers will be displayed as an O-ring under the X-ray; when cross section of the radiopaque markers 2 is shaped as a Double D shown in FIG. 3, the markers will be displayed as a Double D ring under the X-ray; when cross section of the radiopaque markers 2 is shaped as a Cross within a circle shown in FIG. 4, the markers 2 will be displayed as a Cross within a circle under the X-ray; when cross section of the radiopaque markers 2 is shaped as a Tri-chamber shown in FIG. 5, the markers 2 will be displayed as a Tri-chamber within a circle under the X-ray.

Usage (Gastric Motility Detection Method):

Steps: (1) after fasting for 12 hours, the user takes a standard test meal: 80 g instant noodles (with addition of 400 ml water) and 50 g ham sausage, which is finished within 15 minutes; (2) during taking the test meal, the user swallows a piece of detection capsule 100 containing a preset quantity of radiopaque markers 2; (3) after 5 hours, take a plain abdominal radiograph and examine the quantity of residual markers 2 in stomach, and calculate the gastric emptying rate of user based on the residual quantity. Formula for calculating the gastric emptying rate is shown below:

Gastric Emptying Rate=(Preset Quantity of Markers−Residual Quantity of Markers in Stomach)/Preset Quantity of Markers×100%.

Usage (Small Intestinal Motility Detection Method):

Steps: (1) after fasting for 12 hours, the user takes a standard test meal: 80 g instant noodles (with addition of 400 ml water) and 50 g ham sausage, which is finished within 15 minutes; (2) during taking the test meal, the user swallows a piece of detection capsule 100 containing a preset quantity of radiopaque markers 2; (3) after 10 hours, take a plain abdominal radiograph and examine the quantity of residual markers 2 in stomach, and calculate the small intestinal emptying rate of user based on the residual quantity. Formula for calculating the small intestinal emptying rate is shown below:

Small Intestinal Emptying Rate=(Preset Quantity of Markers−Residual Quantity of Markers in Small Intestine)/Preset Quantity of Markers×100%.

Experimental (Colonic Motility Detection Method):

Step 1: (1) Let the user swallow a piece of the detection capsule 100 which in an example contains 24 radiopaque markers 2 and require him/her not to take cathartics, enemas or suppositories within 5 days; (2) take a plain abdominal radiograph on the fifth day to determine the position of markers 2 and the degree of excretion; (3) if at least 80% markers 2 (e.g., ≥19) have been excreted, it can be determined that the colon transit function of the user is normal; (4) if there are 6 or more markers 2 retained in the colon, the user shall accept additional X-ray examination (Contrast Radiography) in the next few days; (5) if the radiopaque markers 2 are deposited in the rectosigmoid colon or the radiopaque markers 2 are retained dispersedly, step 2 shall be performed;

Step 2: (1) if more than 20% radiopaque markers 2 (e.g., 5-6 markers) are retained on the fifth day, let the user take bulk cathartics every day for 1-2 weeks; (2) let the user take a piece of the detection capsule 100 again during the period as described above and take a plain abdominal radiograph again on the fifth to determine the position of radiopaque markers 2 and the degree of excretion; (3) if more than 80% radiopaque markers 2 have been excreted on the fifth day, it can be determined that the colon transit function of the user is normal; (4) if residual radiopaque markers 2 are dispersed in the colon, it can be determined that the user may have insufficient gastrointestinal motility or colonic inertia, and if residual radiopaque markers 2 are deposited in the rectum or rectosigmoid colon, it can be determined that the user may have functional opening delay, such as internal rectal prolapse and pelvic floor achalasia syndrome.

According to the present invention, when the capsule 100 is used for detection of colonic motility, only once or twice plain abdominal X-ray examination can lead to an accurate determination of the colon transit function, which effectively reduce the use of X-ray radiation and thereby reduce damage to user's body due to exposure to radiation.

FIGS. 6-9 are top view of radiopaque markers. In preparation of the radiopaque markers 2 using injection molding or extrusion process, the position of solid X-ray contrast agent in the radiopaque marker 2 is adjusted to make the markers with same shape show different shapes under the X-ray. For example, if the radiopaque markers 2 have a Double D cross section as shown in FIG. 6, and when the solid X-ray contrast agents are adjusted to be only dispersed in the circular ring as shown in FIG. 7, the radiopaque markers 2 will be displayed as an O-ring under the X-ray; when the solid X-ray contrast agents are adjusted to be only dispersed in one of the D cross section as shown in FIG. 8, the radiopaque markers 2 will be displayed as a D-ring under the X-ray; when the solid X-ray contrast agents are adjusted to be only dispersed in the half side of the Double D as shown in FIG. 9, the radiopaque markers 2 will be displayed as an E-ring under the X-ray.

In the methods for detection of gastric motility, small intestinal motility and colonic motility, the detection capsule 100 is used in line with the same method as that in the first embodiment, so further description is unnecessary.

The detection capsule 100, containing the radiopaque markers 2 that are of the same shape but show different shapes under the X-ray, can be used in the segmented detection of colonic motility to detect the transit function of colon. Specific usage is described below (Colonic motility detection by segments):

Steps: (1) Let the user swallow a piece of the detection capsule 100 respectively on the first, second and third day, which in an example contains 24 radiopaque markers 2, and require him/her not to take cathartics, enemas or suppositories within 5 days; (2) take a plain abdominal radiograph on the fourth day: if residual quantity of the radiopaque markers 2 is less than 50, it can be determined that the colonic transit time is normal, and if residual quantity of the radiopaque markers 2 is more than 50, it can be determined that the colonic transit time is abnormal. On the seventh day, take a plain abdominal radiograph again to determine the position of radiopaque markers 2 and the degree of excretion; (3) calculate total quantity of the radiopaque markers 2 in each segment of the colon including ascending colon, descending colon, rectosigmoid colon and transverse colon, and calculate the segmented transit time of colon according to the total quantity of the radiopaque markers 2. For example, the total quantity of radiopaque markers 2 in each segment is equal to transit time in hours; (4) when the total transit time of colon is more than 70 hours and the transit time of any segment is more than or equal to 30 hours, the transit function by segments can be determined to be abnormal.

In the segmented detection of colonic motility, the user shall take orally a piece of the detection capsule 100 every other day in three days. In order to ensure a better detection effect and to distinguish when the radiopaque markers 2 were taken, the position of solid X-ray contrast agents in the radiopaque markers 2 is adjusted to make the markers with same shape show different shapes under the X-ray.

According to the segmented colonic motility detection method in the second embodiment of the present invention, the radiopaque markers 2 in the detection capsule that user takes every day are of the same shape. If the radiopaque markers 2 in the detection capsule 100 come in different shapes, the density may be different and the transit speed in colon may also be different, thus leading to a deviation in results in the detection of colonic motility. Taking the detection capsule 100 in which the radiopaque markers 2 are of the same shape but show different shapes under the X-ray can effectively reduce the deviation in detection results caused by radiopaque markers 2 with different shape and can effectively improve the accuracy of detection results.

Embodiments of preparation of the radiopaque markers 2 are described below. The % are all by weight.

Embodiment 1

In preparation of the radiopaque markers 2, 20% barium sulfate, 45% PVC and 35% auxiliary agents are mixed and injection molded or extruded in a ring-shaped mould to form the radiopaque marker 2. After cleaning and disinfecting, a preset quantity of the radiopaque markers 2 is filled into the capsule enclosure 1 and packed and disinfected to form the detection capsule 100 set forth herein.

Embodiment 2

In preparation of the radiopaque markers 2, 30% barium sulfate, 40% polystyrene and 30% auxiliary agent are mixed and injection molded or extruded in a ring-shaped mould to form the radiopaque marker 2. After cleaning and disinfecting, a preset quantity of radiopaque markers 2 is filled into the capsule enclosure 1 and packed and disinfected to form the detection capsule 100 set forth herein.

Embodiment 3

In preparation of the radiopaque markers 2, 40% barium sulfate, 35% polyethylene and 25% auxiliary agent are mixed and injection molded or extruded in a ring-shaped mould to form the radiopaque marker 2. After cleaning and disinfecting, a preset quantity of radiopaque markers 2 is filled into the capsule enclosure 1 and packed and disinfected to form the detection capsule 100 set forth herein.

Embodiment 4

In preparation of the radiopaque markers 2, 10% bismuth salt, 55% polycarbonate and 35% auxiliary agent are mixed and injection molded or extruded in a ring-shaped mould to form the radiopaque marker 2. After cleaning and disinfecting, a preset quantity of radiopaque markers 2 is filled into the capsule enclosure 1 and packed and disinfected to form the detection capsule 100 set forth herein.

Embodiment 5

In preparation of the radiopaque markers 2, 20% bismuth salt, 50% thermoplastic polyurethane and 30% auxiliary agent are mixed and injection molded or extruded in a ring-shaped mould to form the radiopaque marker 2. After cleaning and disinfecting, a preset quantity of radiopaque markers 2 is filled into the capsule enclosure 1 and packed and disinfected to form the detection capsule 100 set forth herein.

Embodiment 6

In preparation of the radiopaque markers 2, 30% bismuth salt, 45% polypropylene and 25% auxiliary agent are mixed and injection molded or extruded in a ring-shaped mould to form the radiopaque marker 2. After cleaning and disinfecting, a preset quantity of radiopaque markers 2 is filled into the capsule enclosure 1 and packed and disinfected to form the detection capsule 100 set forth herein.

Embodiment 7

In preparation of the radiopaque markers 2, 5% Tungsten, 60% PVC and 35% auxiliary agent are mixed and injection molded or extruded in a ring-shaped mould to form the radiopaque marker 2. After cleaning and disinfecting, a preset quantity of radiopaque markers 2 is filled into the capsule enclosure 1 and packed and disinfected to form the detection capsule 100 set forth herein.

Embodiment 8

In preparation of the radiopaque markers 2, 15% Tungsten, 55% polyethylene and 30% auxiliary agent are mixed and injection molded or extruded in a ring-shaped mould to form the radiopaque marker 2. After cleaning and disinfecting, a preset quantity of radiopaque markers 2 is filled into the capsule enclosure 1 and packed and disinfected to form the detection capsule 100 set forth herein.

Embodiment 9

In preparation of the radiopaque markers 2, 25% Tungsten, 50% polypropylene and 25% auxiliary agent are mixed and injection molded or extruded in a ring-shaped mould to form the radiopaque marker 2. After cleaning and disinfecting, a preset quantity of radiopaque markers 2 is filled into the capsule enclosure 1 and packed and disinfected to form the detection capsule 100 set forth herein.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in particular the matters of shape, size and arrangement of parts within the principles of the present disclosure, up to and including the full extent established by the broad general meaning of the terms used in the claims.

What is claimed is:

1. A capsule, comprises
a capsule enclosure and a present quantity of radiopaque markers filled in the capsule, wherein each radiopaque marker comprises
a solid X-ray contrast agent selected from the group consisting of barium sulfate or bismuth salts and—present at least 10% by weight,
a medical grade plastic with a density less than 1.4 g/cm³ present at least 35% by weight,
and an auxiliary agent between 25%-35% by weight,
wherein the capsule is configured to
detect the motility of stomach, small intestine and colon by examining quantity and location of residual radiopaque markers, and wherein the radiopaque markers feature same appearances but different shapes under the X-ray medical images, by having the solid X-ray contrast agents in the radiopaque markers with different shapes or being placed in different locations; and the density of the radiopaque markers is between 1.0-1.7 g/cm³.

2. The capsule of claim 1, wherein the solid X-ray contrast agent is barium sulfate.

3. The capsule of claim 1, wherein the weight ratio of barium sulfate in the marker is between 20%-40%, the weight ratio of medical grade plastic is between 35%-45% and the weight ratio of auxiliary agent is between 25%-35%.

4. The capsule of claim 1, wherein the medical grade plastics is selected from Polyvinyl chloride (PVC), Polystyrene (PS), Polyethylene (PE), Polypropylene (PP), Polycarbonate (PC), or Thermoplastic polyurethanes (TPU).

5. The capsule of claim 1, wherein the auxiliary agent is selected from lubricants, plasticizers, heat stabilizers, or colorants.

6. The capsule of claim 1, wherein the radiopaque markers are ring shaped markers whose cross-sections are one of the four shapes including O-ring, Double D, Cross and Tri-chamber.

7. The capsule of claim 1, wherein the radiopaque markers are ring shaped markers with a cross section of double D which are shown as O-ring, D-ring or E-ring under the X-ray.

8. The capsule of claim 1, wherein the solid X-ray contrast agent is bismuth salt.

9. The capsule of claim 8, wherein the weight ratio of bismuth salt in the marker is between 10%-30%, the weight ratio of medical grade plastic is between 45%-55% and the weight ratio of auxiliary agent is between 25%-35%.

\* \* \* \* \*